US005549107A

United States Patent [19]

Garraffe et al.

[11] Patent Number: 5,549,107

[45] Date of Patent: Aug. 27, 1996

[54] SECOND STAGE SCUBA DIVING REGULATOR

[75] Inventors: Dean R. Garraffe; Douglas J. Toth, both of Huntington Beach, Calif.

[73] Assignee: Under Sea Industries, Inc., Rancho Dominguez, Calif.

[21] Appl. No.: 512,448

[22] Filed: Aug. 8, 1995

[51] Int. Cl.$^6$ .......................... A62B 7/04; A61M 16/20; F16K 31/00

[52] U.S. Cl. .......................... 128/204.26; 128/205.24; 137/906; 137/908

[58] Field of Search .......................... 128/204.26, 205.24, 128/201.27, 201.28; 137/906, 907, 908; 251/282

[56] References Cited

U.S. PATENT DOCUMENTS

| | | | |
|---|---|---|---|
| 4,094,314 | 6/1978 | Le Cornec | 128/204.26 |
| 4,226,257 | 10/1980 | Trinkwalder | 137/907 X |
| 4,834,086 | 5/1989 | Garofalo | 128/205.24 |
| 4,949,938 | 8/1990 | Ekman | 137/906 X |
| 5,190,030 | 3/1993 | Semeia | 128/204.26 |
| 5,222,490 | 6/1993 | Pmerantz et al. | 128/204.26 |
| 5,233,976 | 8/1993 | Ferguson | 128/204.26 |
| 5,251,618 | 10/1993 | Christianson | 128/205.24 |
| 5,271,428 | 12/1993 | Dunn et al. | 137/509 |

FOREIGN PATENT DOCUMENTS

| | | | |
|---|---|---|---|
| 274076 | 3/1900 | Germany | 137/907 |

*Primary Examiner*—Stephen Funk
*Assistant Examiner*—Eric P. Raciti
*Attorney, Agent, or Firm*—Leonard Tachner; Flam & Flam

[57] ABSTRACT

An improved second stage regulator employs a pneumatically-activated anti-set poppet and inhalation resistance adjustment control knob accessible externally of the regulator. The anti-set poppet utilizes a pressure-activated compression spring to seal the air inlet during exhalation. When the regulator is stored, the relaxed spring permits the seal to withdraw from the sharp edge orifice of the air inlet thereby avoiding seal wear which would otherwise diminish the performance of the regulator. The adjustment control knob permits the diver to modify the required cracking effort by changing the amount of spring compression when the regulator is pressurized.

10 Claims, 1 Drawing Sheet

SECOND STAGE SCUBA DIVING REGULATOR

BACKGROUND OF THE INVENTION

1. Field Of The Invention

The present invention relates generally to scuba diving equipment and more specifically to an improved second stage regulator having a balanced linear flow demand valve with a pneumatically activated anti-set poppet seat and inhalation resistance control adjustment knob.

2. Prior Art

Almost all regulators available today use a soft elastomeric seat inside the second stage demand valve mechanism to seal airflow between breathing cycles. However, when the regulator is unpressurized, such as during storage, the rubber seat sits spring loaded against a sharp edge orifice. Over time, the sharp edge orifice penetrates deeply into the rubber seat, causing the second stage regulator to go out of adjustment, leak air and degrade performance. In addition, in conventional second stage scuba diving regulators, the demand valve mechanism spring load is set at the factory and cannot be varied in the field during use. Consequently, the diver has little if any control over the cracking effort required, that is the effort required to open the demand valve mechanism during each breathing cycle. Normally, the spring load is set at a level which facilitates a normal cracking effort within a limited range of maximum tank pressure variation. However, it would be advantageous if the diver were given some control over the spring load to reduce the cracking effort at low tank pressure or during emergency or high demand conditions, such as at significant depths or for example, when two divers must use the same regulator to breathe.

Thus, there is a need in the scuba diving industry for an improved second stage regulator which provides for spring relaxation as an anti-set feature during non-use of the regulator and which provides the diver with a significant degree of spring load control to modify the cracking effort, particularly at extreme conditions.

A search of the prior art has revealed the following nineteen patents which are deemed to be relevant to the present invention in varying degrees:

| | |
|---|---|
| 3,362,429 | Volsk |
| 4,094,314 | Le Cornec |
| 4,159,717 | Cossey |
| 4,226,257 | Trinkwalder |
| 4,796,618 | Garraffa |
| 4,834,086 | Garofalo |
| 4,889,115 | Bozano |
| 4,971,108 | Gottlieb |
| 5,035,238 | Christianson |
| 5,092,325 | Ainscough |
| 5,222,490 | Pomerantz et al |
| 5,233,976 | Ferguson |
| 5,245,997 | Bartos |
| 5,251,618 | Christianson |
| 5,259,374 | Miller et al |
| 5,259,375 | Schuler |
| 5,265,596 | Sauze |
| 5,343,858 | Winefordner et al |
| RE 31,932 | Christianson |

U.S. Pat. No. 4,834,086 to Garofalo is directed to a second stage regulator for an underwater air breathing apparatus with a floating piston that opens the second stage valve during periods of non-use to prevent distortion of the valve seat and the resultant alteration of calibration. When compressed air is applied to the input fitting 7 of valve 4, a valve seat mounting member 8, a floating piston, is forced by the input air against biasing spring 608 into engagement with the bottom of chamber 204 and seat 508 mounted on the floating piston in gauge valve 3. Breathing by the user opens valve 3 through the action of monostat diaphragm 12 and lever 2. The air flow through valve 4 results in a pressure drop upstream of the floating piston, resulting in spring 608 moving the piston back away from valve 3 increasing the air flow to the user at parity with the inhalation effort.

U.S. Pat. No. 4,094,314 to Le Cornec is directed to a second stage pressure regulator that has a nozzle that is held in operating position by the compressed inlet air and when not in use, the nozzle is only lightly held against the sealing pellet so as to cause no irreversible deformation and maladjustment of the pressure regulator. An intermediate body member 4 holds nozzle 5 that is held lightly by spring 15 against the seat *5a* of the valve member 5. Pressurized air from the first stage regulator applied to the inlet 1 forces the nozzle against the valve seat for normal operation. The valve biased closed by spring 9 is operated by membrane 19 through lever 11.

U.S. Pat. No. 4,159,717 to Cossey is directed to an anti-set protector for second stage scuba regulators. A removable spacer 52 is provided to be interposed between the cover 50 and flexible diaphragm 42 during storage of the regulator. The spacer holds the valve assembly 20 open so that the closure 26 does not take on a compressive set with the resulting loss of sealing ability.

U.S. Pat. No. 5,222,490 to Pomerantz et al is directed to a second stage demand breathing regulator that provides for selective adjustment by the user. The regulator 10 mounted on mouthpiece tube 12, receives pressurized air into conduit 14. Diaphragm 18 deflects responding to changes in air pressure and opens valve 32 through lever 28. Valve seat 36 and retainer 37 are formed of metal so as to withstand the inlet pressure without deforming. Knob 52 is provided for positioning spring retainer 46 to and fro so as to adjust the bias on the pressure regulating spring 40 for a user selected limited adjustment. During assembly, the valve seat 36 is adjusted by means of the relatively fine screw threads of retainer 37.

U.S. Pat. No. 5,035,238 to Christianson is directed to a second stage regulator for scuba that incorporates a semi-balanced valve mechanism that includes an external adjustment knob for the diver to change the regulator's sensitivity to conserve gas. The second stage regulator 14 with outer case 15, incorporates a diaphragm 17, exhaust valve 21, purge button 22, whisker lever 25 and valve mechanism 26. External adjusting knob 34 provided on valve mechanism 26 has fine threads 35 to adjust the bias on pressure regulating spring 54 and thereby the force applied to the sealing seat 44 against edge 40. The diver can adjust the knob to change the regulator's inhalation sensitivity during special circumstances.

U.S. Pat. No. 5,259,375 to Schuler is directed to a second stage scuba regulator with a diver/user air volume control adjustment. The regulator 10, with a balanced piston breathing apparatus 26, operated by a lever 28 and diaphragm 32, has an air volume control 100 that is independent of the selected resistance. Air volume control 100 has knob 110 provided to screw in stem 102 to vary the occlusion of discharge opening 72, thereby varying the volume of air supplied independent of the selected resistance.

U.S. Pat. No. Re. 31,932 to Christianson is directed to a second stage demand regulator with a user adjustable aspiration control and having a diaphragm that flattens against a platform so as to exhibit a varying effective area resulting in stable operation. The regulator 10 with flow control valve 19 and diaphragm assembly 22 has a rotatable cap 60 that changes the location of aspiration opening 57', thereby adjusting the amount of aspiration provided by the regulator.

U.S. Pat. No. 4,971,108 to Gottlieb is directed to a compact second stage inhalation responsive regulator with a user adjustable inhalation force control. The generally tubular regulator has a cylindrical diaphragm end cage that operates inlet air valve 44 through center post 52. An alternate embodiment, shown in FIG. 9 has an adjusting screw 72 that supports and biases valve spring 50. Changing the bias on the valve spring adjusts the amount of inhalation force necessary to open the valve. From the aforementioned prior art description it will be seen that there is apparently no known prior art which provides an anti-set spring relaxation feature and a spring load control feature in a second stage scuba diving regulator. There is therefore a continuing need for an improved second stage scuba diving regulator of the type having a balanced linear flow demand valve but with a pneumatically activated anti-set poppet seat and an inhalation resistance control adjustment knob.

SUMMARY OF THE INVENTION

In the present invention, when the second stage regulator thereof is unpressurized, such as in periods of storage or non-use, the poppet assembly has little or no force applied to it to press it against the sharp edge orifice. During use, as soon as the interior of the regulator is pressurized, the anti-set poppet operates by using incoming air pressure from the first stage to move the poppet assembly forward to its working position to make contact with the sharp orifice. In this manner, the sharp orifice only makes contact with the rubber seat during actual use. This eliminates the deep impressions left by the orifice during periods of non-use. A light or reduced force may remain on the poppet to keep it in the proximity of or just touching the orifice when the regulator chamber is unpressurized. A scuba regulator with such an anti-set feature will have a longer service life and a drastically improved performance consistency.

Once the regulator has been pressurized, a spring adjustment knob can be externally rotated at a threaded connection of the regulator. As the spring adjustment knob is rotated in or out, the load height of a balance chamber spring is varied. If the spring is shortened, the cracking effort in the regulator is increased due to the higher spring load. If the knob is retracted, that is, if the spring is lengthened, the cracking effort is decreased due to the lower spring rate. The spring adjustment knob is a means to limit travel of the balance chamber within the regulator and to control the spring load by manually rotating the adjustment in or out to increase or decrease the inhalation cracking force, respectively.

OBJECTS OF THE INVENTION

It is therefore a principal object of the present invention to provide an improved second stage regulator for scuba diving, the regulator having both an anti-set poppet and an external cracking-effort-control adjustment to permit the diver to vary the cracking effort manually during the dive.

It is an additional object of the present invention to provide an improved second stage regulator for scuba diving having a balanced linear flow demand valve with a pneumatically activated balanced poppet wherein a soft elastomeric seal engages a sharp-edge orifice only when the interior chamber of the regulator is pressurized and relaxes the seal from the orifice edge when the interior chamber of the regulator is unpressurized.

It is still an additional object of the present invention to provide an improved second stage regulator for scuba diving wherein an externally adjustable control knob permits the diver to vary the load of a spring controlling the resistance to unsealing a poppet seal from an orifice edge when the interior chamber of the regulator is pressurized so that the diver can vary the cracking effort required during breathing cycles, particularly at high demand periods and during low tank pressures.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawings in which.

DETAILED DESCRIPTION OF A PREFERRED EMBODIMENT

Figure 1:
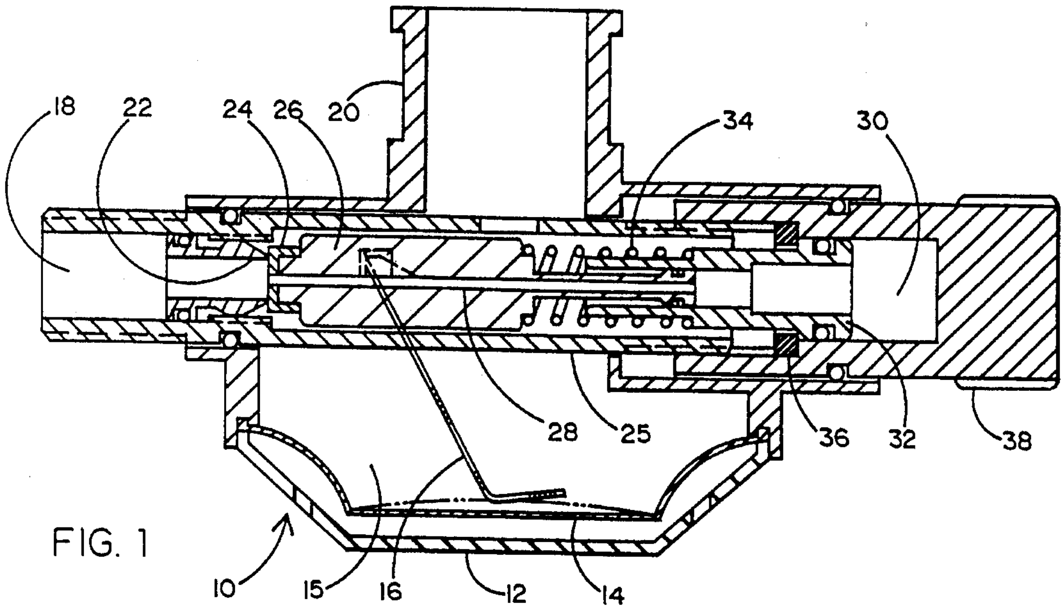
FIG. 1 is a cross-sectional view of the regulator of the present invention shown in its pressurized configuration.

Referring now to the accompanying figures, it will be seen that a second stage regulator 10 comprises a housing 12, a diaphragm 14 forming an interior chamber 15 and a lever 16 connected to an air inlet 18. Also provided is a mouthpiece 20 whereby the second stage regulator 10 may be held in the mouth of a diver for breathing during the dive. The air inlet 18 is connected to a first stage regulator and pressure cylinder (not shown) in a conventional manner. High pressure air from the cylinder is reduced to approximately 135 psi over ambient pressure by the regulator first stage. Air travels through a low pressure air hose and into the air inlet 18.

Air travels through a sharp edge orifice 22 and into the soft elastomeric seal 24 which is mounted at the end of a poppet 26. As air continues through an air barrel 25 in which the poppet 26 is mounted and particularly through an air passage 28 which is positioned axially along the poppet 26, it communicates with and fills a balance chamber 30 at the opposite end of the air barrel 25. In this manner, the pressure chamber 30 also becomes pressurized to 135 psi. More specifically, as pressure builds up in the pressurized chamber 30, the force of the air pressure begins to move a sliding spring seat 32 until a spring seat stop 36 is engaged. Such engagement sets the correct spring force to seal the poppet seat or elastomeric seal 24 against the sharp edge orifice 22, thus setting the proper cracking or opening force of the demand valve for normal conditions.

As the air is required by the scuba diver, air is drawn by the diver by inhalation directly at the mouthpiece 20. This demand creates a pressure drop inside the chamber 15, causing the diaphragm 14 to bow inwardly, thereby engaging and moving lever 16 in a direction which causes the poppet 26 to unseat the seal 24 from the sharp orifice 22, thereby allowing air to flow into the regulator in the manner described above.

Figure 2:
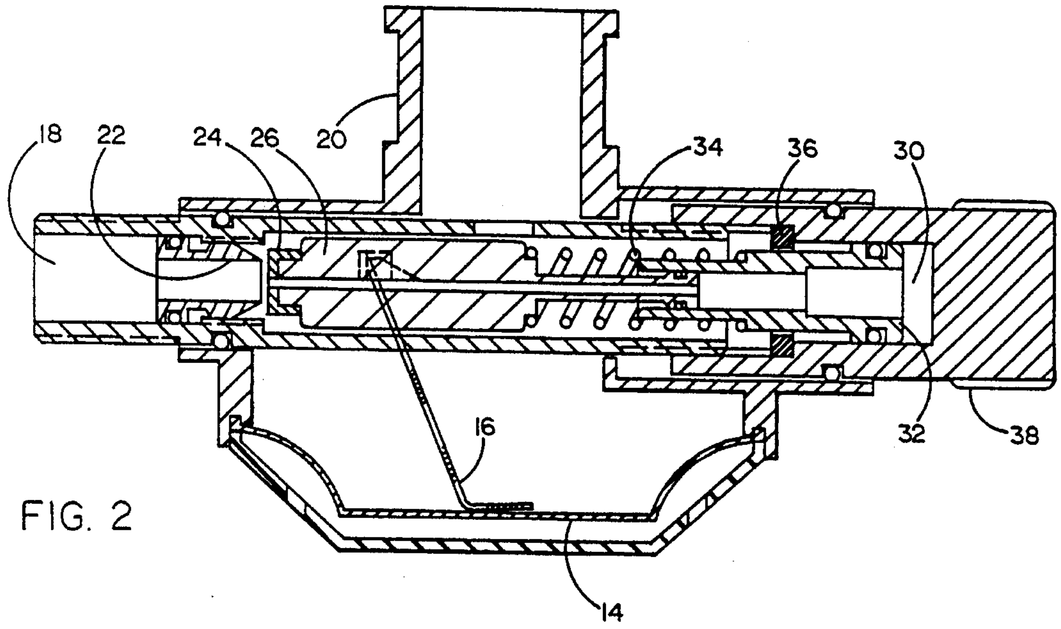
FIG. 2 is a cross-sectional view of the regulator of the present invention shown in its unpressurized configuration.

Referring now to FIG. 2, it will be seen that an unpressurized regulator has no air pressure in the pressure chamber 30. Consequently, the sliding spring seat 32 has retracted rearwardly, allowing the spring 34 to relax to a predetermined length which substantially reduces the applied force of contact between the sharp edge orifice 22 and elastomeric seal 24. In fact, as seen in FIG. 2, the elastomeric seal may be removed entirely from contacting the orifice, thus entirely disengaging those two surface as shown in FIG. 2. Accordingly, it will be seen that the unpressurized improved regulator of the present invention is configured so that the poppet assembly has no force applied to it to press it against the sharp edge orifice. As a consequence, deep impressions otherwise left by the sharp edged orifice on the elastomeric seal of the prior art during periods of non-use, are obviated in the present invention. It will be understood that the spring and poppet geometry may be varied to permit a very light, reduced force to remain on the poppet to keep it in proximity of or just touching the orifice when the regulator is unpressurized.

An additional feature of the present invention is the inhalation adjustment setting feature which can be used to vary the cracking effort to make it either greater or smaller. Those conditions where the cracking effort may be advantageously reduced have been previously mentioned, namely, during low tank pressure conditions, as well as during certain high demand operations at great depth, or for example during emergencies where two divers must use the same regulator while surfacing. Under some diving conditions, it may be necessary to change the inhalation resistance cracking effort in the opposite direction. For example, if the diver is working in a head down position, the cracking effort can be advantageously adjusted for harder breathing to prevent the uncomfortable condition of overfilling the diver's lungs. In addition, when going through the surf on heavy currents the ability to externally stiffen the cracking effort helps to stabilize the regulator sensitivity.

The ability to adjust the cracking effort externally in the regulator of the present invention may be understood by referring to the accompanying figures wherein it will be seen that a spring adjustment knob 38 is provided on the air barrel 25 at the end opposite the air inlet 18. Once the regulator 10 has been pressurized, the spring adjustment knob 38 may be externally rotated either in or out from its threaded connection with the air barrel 25. As the spring adjustment knob 38 is rotated in or out, the balance chamber 30 stays positioned against the spring stop seat 36, due to the 135 psi air pressure force in the chamber 30 pressing on the balance spring 34. If the spring is shortened, the cracking effort is increased due to the higher spring load. This occurs when the knob is rotated in a direction to extend it into the air barrel 25. On the other hand, if the knob 38 is retracted from the air barrel 25, the spring 34 is lengthened and the cracking effort is decreased due to the lower spring rate. The adjustment knob 38 is therefore a means to limit travel of sliding spring seat 32 and thus adjust the size or volume of the balance chamber and to control the spring load by manually rotating the adjustment knob in or out to increase or decrease the inhalation cracking force, respectively.

Having thus described an exemplary embodiment of the best mode of carrying out this invention, what we claim is:

1. A pneumatically activated second stage scuba diving regulator having a flow demand valve responsive to inhalation by a diver creating a partial vacuum within a chamber of the regulator to withdraw a balanced poppet, having a seal, from the edge of an orifice in fluid communication with a source of pressurized air to fill said regulator with the air; the regulator comprising:

an air barrel having a first end with an inlet connected to said air source and a second end with a threaded, externally adjustable knob connected thereto;

said poppet contained within said air barrel and moveable along the longitudinal axis of said air barrel to either compress said seal against said orifice edge or to withdraw said seal from said orifice edge;

a spring positioned around said poppet in coaxial engagement therewith and a slidable spring seat balance device receiving said poppet opposite said seal and positioned for forming a balance chamber within said air barrel adjacent said adjustable knob and for selectively compressing said spring in response to air pressure within said balance chamber; and an air channel extending through said poppet and said balance device for feeding air from said inlet to said balance chamber to compress said spring facing said seal against said orifice.

2. The regulator recited in claim 1 wherein said spring, poppet and balance device are configured to withdraw said poppet seal from said orifice edge upon removal of air pressure from said inlet.

3. The regulator recited in claim 1 wherein said externally adjustable knob is configured for altering the maximum compression of said spring for changing the force of engagement between said poppet seal and said orifice edge.

4. The regulator recited in claim 3 wherein said knob and said balance device have respective stops for said changing of said maximum compression in response to said knob.

5. The regulator recited in claim 1 further comprising a mouthpiece and an air path between said air barrel and said mouthpiece for directing pressurized air into said mouthpiece upon withdrawal of said poppet by said demand valve.

6. A pneumatically activated second stage scuba diving regulator having a flow demand valve responsive to inhalation by a diver creating a partial vacuum within a chamber of the regulator to withdraw a balanced poppet, having a seal, from the edge of an orifice in fluid communication with a source of pressurized air to fill said regulator with the air; the regulator comprising:

an air barrel having a first end with an inlet connected to said air source and a second end having an enclosed chamber in communication with said inlet;

said poppet contained within said air barrel and moveable along the longitudinal axis of said air barrel to either compress said seal against said orifice edge or to withdraw said seal from said orifice edge;

a spring positioned around said poppet in coaxial engagement therewith and a slidable spring seat balance device receiving said poppet opposite said seal and positioned for forming a balance chamber within said air barrel adjacent said second end and for selectively compressing said spring in response to air pressure within said balance chamber; and an air channel extending through said poppet and said balance device for feeding air from said inlet to said balance chamber to compress said spring facing said seal against said orifice.

7. The regulator recited in claim 6 wherein said spring, poppet and balance device are configured to withdraw said poppet seal from said orifice edge upon removal of air pressure from said inlet.

8. The regulator recited in claim 6 further comprising an externally adjustable knob threadably connected to said second end of said air barrel for altering the maximum compression of said spring for changing the force of engagement between said poppet seal and said orifice edge.

9. The regulator recited in claim 8 wherein said knob and said balance device have respective stops for said changing of said maximum compression in response to said knob.

10. The regulator recited in claim 6 further comprising a mouthpiece and an air path between said air barrel and said mouthpiece for directing pressurized air into said mouthpiece upon withdrawal of said poppet by said demand valve.

* * * * *